United States Patent [19]

Poupon

[11] Patent Number: 4,859,660

[45] Date of Patent: Aug. 22, 1989

[54] METHOD OF TREATING CIRRHOSIS

[75] Inventor: Raoul Poupon, Paris, France

[73] Assignee: Synthelabo, Paris, France

[21] Appl. No.: 122,867

[22] Filed: Nov. 19, 1987

[30] Foreign Application Priority Data

Nov. 20, 1986 [FR] France .................................. 86 16139

[51] Int. Cl.$^4$ .......................... A61K 31/56; C07J 1/00
[52] U.S. Cl. .................................. 514/182; 260/397.1
[58] Field of Search ...................... 260/397.1; 514/182

[56] References Cited

U.S. PATENT DOCUMENTS 4,083,994 4/1978 Noda et al. ......................... 514/546

OTHER PUBLICATIONS

Chemical Abstracts, vol. 101 (1984), #104084a; Mukata et al.
French Vidal Dictionary, p. 1659, "Ursolvan".
Merck Index, 9695, 10th Ed., 1983, p. 1413.

*Primary Examiner*—Leonard Schenkman
*Assistant Examiner*—Joseph A. Lipovsky
*Attorney, Agent, or Firm*—Fleit, Jacobson, Cohn, Price, Holman & Stern

[57] ABSTRACT

A method of treating primary biliary cirrhosis comprising administering ursodeoxycholic acid to a patient suffering therefrom.

4 Claims, No Drawings

METHOD OF TREATING CIRRHOSIS

The present invention relates to the treatment of primary biliary cirrhosis.

Ursodeoxycholic acid is a known compund that has been used for the dissolving treatment of cholesterolic biliary lithiasis. It has now been found that ursodeoxycholic acid also acts effectively in the treatment of primary biliary cirrhosis (PBC).

PBC is a deadly disease. PBC is said to be "primary" because it is not induced by alcohol abuse or drugs or infectious hepatitis.

PBC afflicts mainly middle aged women. It is a disease in which small biliary intrahepatic vessels are progressively destroyed.

The evolution of the disease varies, usually between 5 and 10 years. The symptomatology starts with fatigue, itching followed by increased liver size and icterus. Hepatic transplantation is the only long term survival means as yet.

Up to now it was thought that the disease was an autoimmune one because mitochondrial antibodies were observed in the patients. This is why all the treatments used so far have been immunosuppressive, such as high doses of corticoids and azathioprine.

The present invention based upon ursodeoxycholic acid hinges on the hypothesis that the symptomatology and the extent of the disease are not immunological, but are due to the toxicity of the biliary acids synthesized by the liver. These acids are involved in the lipids metabolism. The biliary acids are involved in a closed cycle of elimination by the bile and reabsorption by the intestine.

When administered chronically, ursodeoxycholic acid, which is non-toxic, substitutes itself for these biliary acids which allows the elimination from the body.

After administration of 13 to 15 mg/kg/day of ursodeoxycholic acid to patients for 2 years, the total concentration of serum bile acids was unaltered; the percentage of patients having pruritus fell from 53 to 8%; the patients' blood bilirubin concentration became less than 34 $\mu$M; the serum alkaline phosphatase, transaminase and $\gamma$-glutamyltransferase activities decreased in all the patients; and the levels of prothrombin, albumin, $\gamma$-globulins and immunoglobulins M were unaltered.

Results obtained during the last 5 years confirm previous results. With increased numbers of patients, it can be shown that the therapeutic effect increases with time and with no adverse effects.

The ursodeoxycholic acid may be administered to a patient in association with any suitable excipient. Preferably, the ursodeoxycholic acid is administered orally, for example, in capsule form. An example of a suitable formulation in the form of a gelatin capsule is as follows:

ursodeoxycholic acid 200 mg;

excipient: magnesium stearate, talc, Amijel corn starch;

gelatin capsule: gelatin, titanium dioxide, indigotin, sulphur dioxide.

I claim:

1. A method of treating primary biliary cirrhosis which comprises administering an effective amount of ursodeoxycholic acid to a patient suffering from primary biliary cirrhosis.

2. A method according to claim 1 wherein 13 to 15 mg/kg/day of ursodeoxycholic acid is administered to the patient.

3. A method according to claim 1 wherein the ursodeoxycholic acid is administered orally.

4. A method according to claim 3 wherein the ursodeoxycholic acid is administered in the form of gelatin capsules.

* * * * *